(12) United States Patent
Nakamura

(10) Patent No.: US 7,551,270 B2
(45) Date of Patent: Jun. 23, 2009

(54) DIFFERENTIAL REFRACTIVE INDEX DETECTOR

(75) Inventor: Takafumi Nakamura, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 113 days.

(21) Appl. No.: 11/765,848

(22) Filed: Jun. 20, 2007

(65) Prior Publication Data

US 2008/0024770 A1 Jan. 31, 2008

(30) Foreign Application Priority Data

Jul. 28, 2006 (JP) .............................. 2006-205796

(51) Int. Cl.
*G01N 21/41* (2006.01)
*G01N 30/02* (2006.01)
*G01N 1/00* (2006.01)
*G01N 30/00* (2006.01)
*B01D 15/08* (2006.01)

(52) U.S. Cl. .................... 356/130; 356/131; 210/198.2; 210/656; 73/61.52; 73/61.56; 73/61.57

(58) Field of Classification Search ........................ None
See application file for complete search history.

(56) References Cited

U.S. PATENT DOCUMENTS 2,881,118 A * 4/1959 Spann et al. ................ 202/160
5,398,110 A * 3/1995 Kitaoka ....................... 356/130
6,295,125 B1 * 9/2001 Tokieda et al. .............. 356/130
2007/0076192 A1 * 4/2007 Nakamura ................... 356/131

FOREIGN PATENT DOCUMENTS

| JP | 2-10248 | 1/1990 |
|---|---|---|
| JP | 3-162651 | 7/1991 |
| JP | 4-24540 | 1/1992 |
| JP | 5-288676 | 11/1993 |
| JP | 2504356 | 11/1993 |
| JP | 2006-162262 | 6/2006 |

* cited by examiner

*Primary Examiner*—Gregory J Toatley, Jr.
*Assistant Examiner*—Gordon J Stock, Jr.
(74) *Attorney, Agent, or Firm*—J.C. Patents

(57) ABSTRACT

Provided is a differential refractive index detector having a light receiving element, a zero glass, a zero glass driving unit and a storing portion, and is capable of performing purging operation thoroughly based on a unified standard. The light receiving element receives a measuring light passing through cells (S, R) to generate a slit image. The zero glass makes the slit image parallelly move on the light receiving element. The zero glass driving unit makes the zero glass rotate. The storing portion stores a rotating angle of the zero glass when the same solution fills up the two cells (S, R). When a purging operation for replacing a reference solution in the flow cell is performed, the stored rotating angle is taken as a standard value for being compared with a current rotating angle of the zero glass. If the two angles are the same, the purging operation is finished.

10 Claims, 2 Drawing Sheets

DIFFERENTIAL REFRACTIVE INDEX DETECTOR

CROSS-REFERENCE TO RELATED APPLICATION

This application claims the priority benefit of Japanese application serial no. 2006-205796, filed Jul. 28, 2006. All disclosure of the Japanese application is incorporated herein by reference.

BACKGROUND OF THE INVENTION

1. Field of the Invention

The present invention relates to a differential refractive index detector used as a detector in an analysis device such as a liquid chromatograph.

2. Description of Related Art

A differential refractive index detector includes a flow cell, a light receiving element and an optical system. The flow cell has two cells spaced apart by a spacer inclined with respect to an optical axis of a measuring light. A sample solution passes through one cell, and a reference solution passes through the other cell. The light receiving element receives the measuring light refracted by the flow cell. The optical system makes the measuring light pass through a slit to irradiate into the flow cell, and guides the measuring light from the flow cell to the light receiving element, and thus forming a slit image on the light receiving element. And, the differential refractive index detector detects the refractive index variation of the sample solution according to a displacement of the slit image on the light receiving element.

FIG. 3 is a schematic view of an example of the differential refractive index detector. A light emitted from a light source 8 passes through a slit 10 to become a measuring light 12. Next, after passing through a lens 14 disposed in front of a flow cell 16, the measuring light 12 is irradiated on the flow cell 16. The flow cell 16 includes two cells S and R, and the cells S and R are spaced apart by a spacer 18. The cell S includes a liquid inlet 22i and a liquid outlet 22o, and the cell R includes a liquid inlet 24i and a liquid outlet 24o. A reflecting mirror 26 is disposed behind the flow cell 16. After being reflected by the reflecting mirror 26, the measuring light already transmitting through the flow cell 16 will re-transmit through the flow cell 16. The reflected light, from the reflecting mirror 26 and transmitting through the flow cell 16, will images on the light receiving element 30 through the lens 14, so as to generate a slit image. A light receiving surface of the light receiving element 30 is divided into two parts, and the slit image is generated in a manner of crossing each region of the light receiving element 30 that is divided into two parts. A zero glass 28 is disposed on a light path between the lens 14 and the light receiving element 30. The zero glass 28 is used to make the slit image to parallelly move on the light receiving element 30. A pulse motor 32 is used to drive the zero glass 28 to rotate, and the pulse motor 32 rotates according to signals from a control and calculation portion 34. According to the rotating angle at this time, the zero glass 28 makes the slit image to parallelly move on the light receiving element 30. A signal processing circuit 36 executes a signal processes to obtain the refractive index variation according to a detecting signal from the light receiving element 30, and the control and calculation portion 34 is used as the differential refractive index detector to obtain an output value.

The refractive index of a substance greatly depends on the temperature, so the temperature dependence varies comply with different substances. Therefore, as for the differential refractive index detector, practically, before a sample is analyzed, the content fluid in the cell (S) which the sample solution passes through and in the cell (R) which the reference solution passes through must be replaced thoroughly. Particularly, when the composition of the mobile phase is changed, it is necessary to adopt a following flow path that is capable of replacing (purging) the content fluid in the cell R. The flow path connected with the flow cell 16 has the following structure, that is, a structure capable of being switched between the analysis process and the purging operation. More specifically, a following flow path is formed during the analysis process, i.e., the outflow liquid from a column (not shown) enters the cell S from the liquid inlet 22i, and outflows from the liquid outlet 22o. And, a following flow path is formed during the purging operation, i.e., the outflow liquid from the column is from the liquid outlet 22o and flows into the cell R through the liquid inlet 24i, and then outflows from the liquid outlet 24o. Therefore, during the analysis process, the mobile phase used for analysis and the sample solution flow into the cell S, and the mobile phase is stored in the cell R. During the purging operation, the cell S and the cell R are mutually communicated, and the mobile phase used for analysis flows into the cell S and the cell R.

When air bubbles are generated in the cell or the composition of the mobile phase is changed, the purging operation must be performed. If the purging is not sufficient, the output value easily changes as the changing of the temperature, such that the detector cannot sufficiently achieve its functions.

In conventional art, any one of the following three methods is used to perform the purging operation. Firstly, the method used by the operator to perform the purging operation manually is that (1) a liquid supply device connected to the differential refractive index detector is used to supply the liquid for a suitable time period under a suitable condition, and then, assures that the output of the differential refractive index detector becomes stable on the frame of a data processing device. In addition, the method of automatically performing the purging operation is that (2) the purging operation is performed for a preset time, and after the above time period, the purging operation is automatically finished (Patent reference 1); (3) the purging operation is performed with a preset volume, and after the liquid supply device has finished supplying the above volume of liquid, the purging operation is finished.

[Patent reference 1] Japanese Laid-Open Patent Publication 2001-033386.

The above three methods have the following defects. According to the method (1), it needs an operator to execute the operation, and under most cases, the operator may waste the time till the purging process finished. Also, when determining whether the purging is sufficiently performed or not, there is always less information for making judgment, so in most cases, it depends on experiences of the operator. And thus, the standard used for the judgment varies from person to person. According to the method (2), the purging operation is automatically finished after during the specified time, so as to reduce the problems relevant to time of the method (1). However, the flow of the liquid passing through the flow cell or the composition of the purging liquid the purged liquid is different, so the purging degree that has been finished in the specified time may be different. In addition, in the purging operation process, due to certain poor situations such as the liquid used for purging is not sufficient, even if the purging is substantially not performed, the purging operation is finished after the specified time. According to the method (3), after the liquid of the set volume has been delivered, the purging operation is automatically finished, so as to reduce the problems relevant to time. However, it is the same as (2) that the purging degree varies depend upon different conditions, and even under the poor situations, the purging operation is still finished.

FIG. 4 is a schematic view of the relation between the purging degree and the rotating angle of the zero glass. The zero glass 28 is rotated, such that the slit image is generated in a manner of crossing each region of the light receiving element 30 that is divided into two parts. As shown in FIG. 4(a), if the purging operation is sufficiently performed in the flow cell with the temperature maintained to be uniform (e.g., 40° C.), the compositions of the content fluid in the cells S and R become completely the same. However, if the purging operation is not sufficient, the compositions of the content fluid in the cells S and R are different from each other, and the refraction will occur on the interface of the cell S/cell R, such that the slit image is biased from the optical axis (as shown in FIG. 4(b)). And then, the zero glass 28 is rotated to make the slit image to parallelly move on the light receiving element 30, so as to correct the bias of the slit image. Therefore, the slit image is uniformly imaged on the region of the light receiving element 30 divided into two parts (the midmost position). It can be viewed from the appearance that, the purging operation is sufficiently performed.

SUMMARY OF THE INVENTION

Accordingly, the present invention is directed to a differential refractive index detector, and a liquid chromatograph device using the same. The differential refractive index detector is confirmed to be stable till the state that the analysis process S can be performed, so as to avoid the effect of the personal difference in terms of determining the stable state, and thus effectively performing the analysis operation.

In view of the above problems, the present invention provides a differential refractive index detector, which includes a light receiving element, a zero glass, a zero glass driving unit and a storing portion. The light receiving element receives a measuring light to generate a slit image, in which the measuring light is made to pass through a slit to reach a flow cell for being transmitted as a transmitted light. Then, by means of being reflected by a reflecting mirror, the transmitted light is made to re-transmit through the flow cell. In the flow cell, a sample solution passes through one cell of two cells spaced apart by a spacer inclined with respect to an optical axis of the measuring light, and a reference solution passes through the other cell. The zero glass makes the slit image parallelly move on the light receiving element. The zero glass driving unit makes the zero glass rotate. The storing portion stores a rotating angle of the zero glass when the same solution fills up the two cells. Furthermore, the differential refractive index detector further includes a determining portion, for comparing a current angle of the zero glass with the rotating angle of the zero glass stored in the storing portion when a purging operation of replacing the reference solution in the flow cell is performed. If the difference between the two angles falls into a specified range, the purging operation is finished.

Alternatively, the present invention provides a purging method for purging the flow cell of the differential refractive index detector. The differential refractive index detector includes a light receiving element, a zero glass and a zero glass driving unit. The light receiving element receives a measuring light to generate a slit image, in which the measuring light is made to pass through a slit to reach a flow cell for being transmitted as a transmitted light. Then, by means of being reflected by a reflecting mirror, the transmitted light is made to re-transmit through the flow cell. In the flow cell, a sample solution passes through one cell of two cells spaced apart by a spacer inclined with respect to an optical axis of the measuring light, and a reference solution passes through the other cell. The zero glass makes the slit image parallelly move on the light receiving element. The zero glass driving unit makes the zero glass rotate. The purging method is characterized in storing a rotating angle of the zero glass in a storing portion when the same solution fills up the two cells. When a purging operation of replacing the reference solution in the flow cell is performed, a current angle of the zero glass is compared with the rotating angle of the zero glass stored in the storing portion. If the difference between the two angles falls into a specified range, the purging operation is finished.

By adopting the above constitution, under the state of thoroughly purging, i.e., under the state that the same solution fills up each cells spaced apart by the spacer, the rotating angle of the zero glass is stored. When the purging degree is determined, the stored rotating angle is used as a standard value. Then, according to the standard value, it is determined whether the purging operation should be finished or not. Here, the rotating angle is not only a numerical number for representing the angle, and even the rotating angle is considered as a pulse number for the pulse motor to drive the predetermined angle, the same effect can be obtained.

The rotating angle of the zero glass under the state that the same solution fills up each cells spaced apart by the spacer is stored, and the stored rotating angle is compared with the current rotating angle of the zero glass in the purging operation, so as to determine the purging degree. Therefore, it is not necessary to artificially determine the purging degree by an operator, so as to realize the purging state at the unified standard. The purging operation is executed until the standard is satisfied, so that the purging operation can be thoroughly performed without depending on a composition of the purging/purged liquid or flow of thereof. In addition, the determination is not made according to the time variation of the refractive index, so even if it is impossible to detect the time variation of the refractive index due to exceeding the lower limit or the upper limit of the tested limit, the purging operation can be practically performed without mis-determining that the purging operation has already been finished. If the differential refractive index detector is adopted to be used as the detector of a liquid chromatograph, the analysis can be performed under the condition that the purging operation is practically performed thoroughly, so as to obtain data with high reliability.

In order to make the aforementioned and other objects, features and advantages of the present invention comprehensible, preferred embodiments accompanied with figures are described in detail below.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

The differential refractive index detector of the present invention is illustrated below with reference to the accompanying drawings.

Figure 1:
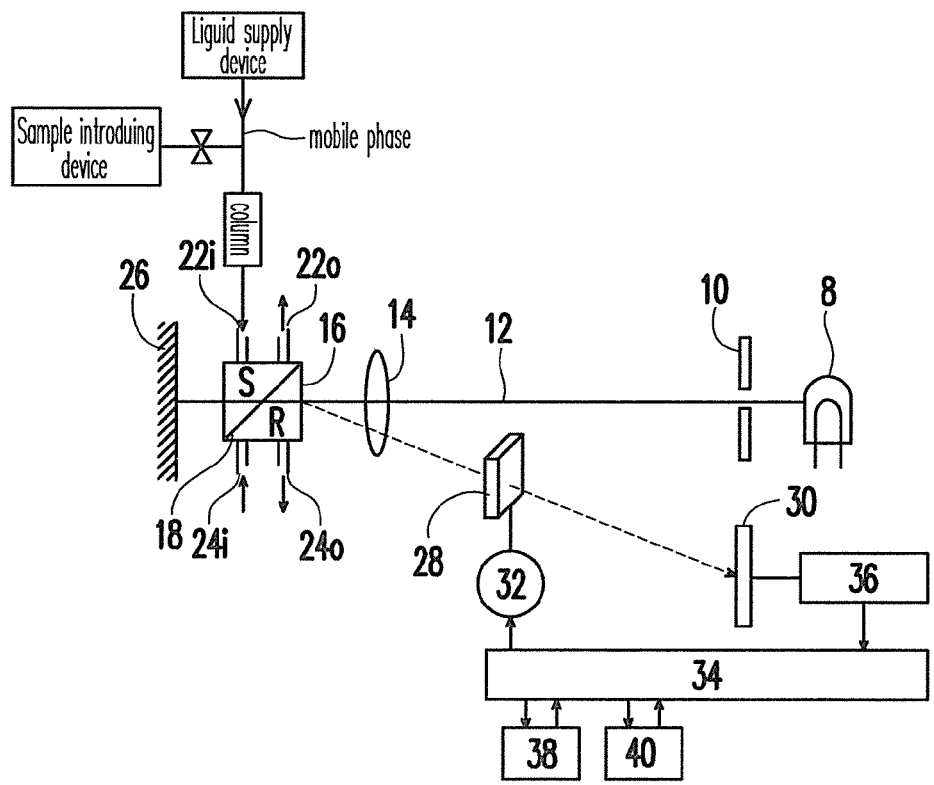
FIG. 1 is a schematic view of a differential refractive index detector structure of the present invention.
Figure 4:
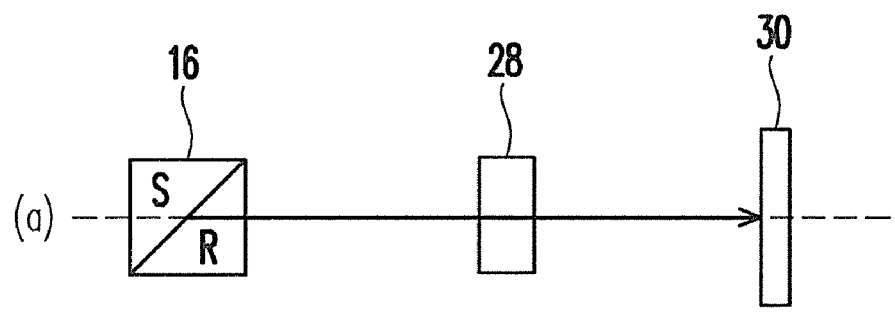
FIG. 4 is a schematic view of the relation between the purging degree and the rotating angle of the zero glass.
Figure 4:
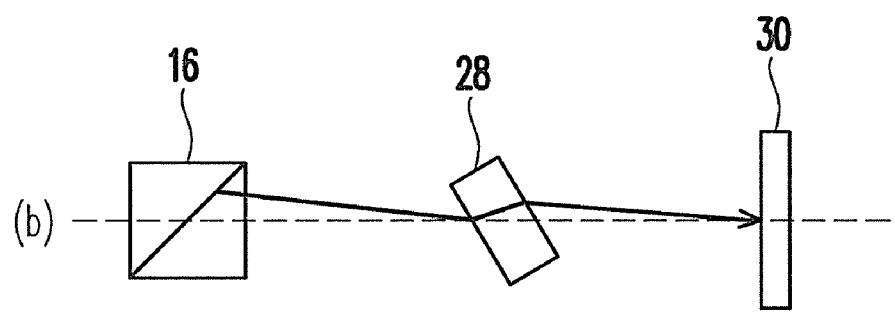

FIG. 1 is a schematic view of a differential refractive index detector structure of the present invention. As compared with the conventional differential refractive index detector shown in FIG. 4, the differential refractive index detector in the present invention further includes a storing portion 38 for storing the rotating angle of a zero glass 28. When the same solution fills up the two cells (S and R), a rotating angle of the zero glass 28 making the slit image to be generated at the midmost position on the light receiving element 30 is stored in the storing portion 38 and taken as a standard value for determining whether the purging operation is thoroughly performed or not. In addition, the differential refractive index detector includes a determining portion 40 for comparing the rotating angle stored in the storing portion 38 with a current rotating angle.

When the cell S and the cell R are filled up by the liquid with same composition, the refraction does not occur on the interface of the cell S/cell R. Therefore, as long as the composition of the mobile phase is the same, the rotating angle of the zero glass 28 for making the slit image to be generated at the midmost position on the light receiving element 30 is fixed. Thus, when only one mobile phase is used and once the standard value is stored in the storing portion 38, the standard value is used as the reference, so it is not necessary to reset the standard value. When air bubbles are generated in the cell R or the reference solution is replaced, the standard value is used to perform the purging operation.

Figure 2:
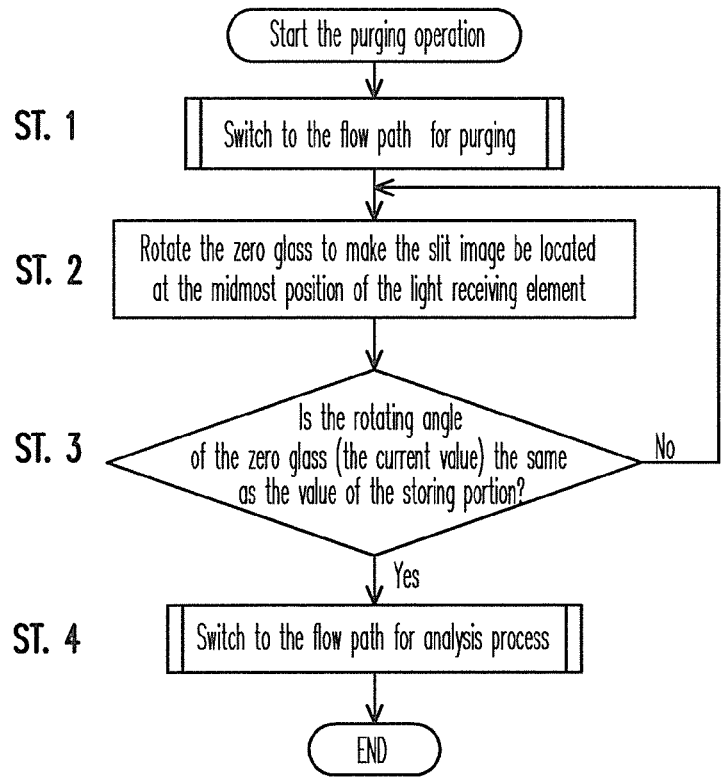
FIG. 2 is a flow chart of the sequence adjusting process for the differential refractive index detector of the present invention.
Figure 3:
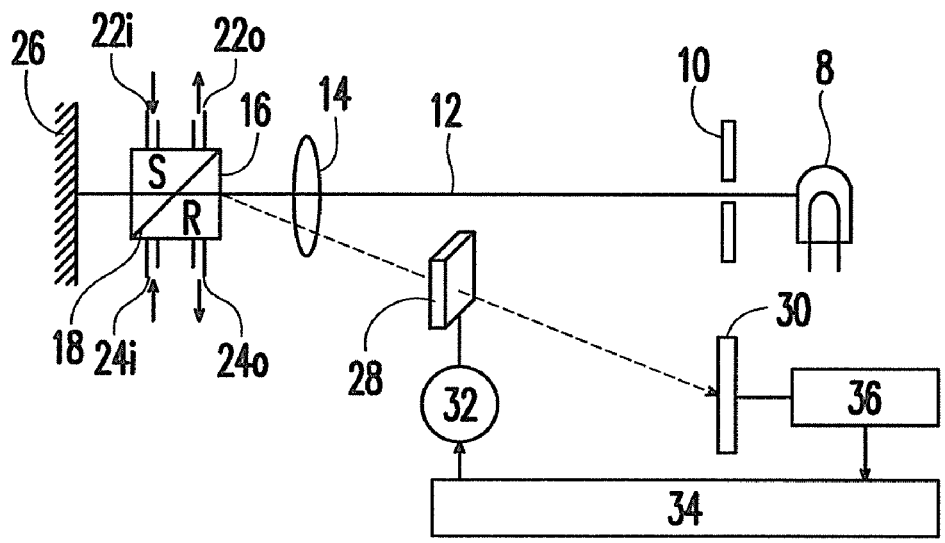
FIG. 3 is a schematic view of a differential refractive index detector structure of the conventional art.

FIG. 2 is a flow chart of a purging operation of the differential refractive index detector of the present invention. In the differential refractive index detector of the present invention, after the purging operation is started, the flow path of the differential refractive index detector is switched to a flow path for purging (ST.1). Upon forming the flow path for purging, the liquid supplied from the liquid supply device can sequentially replace the content fluid in the cell S and the cell R.

When the supplied liquid is used to replace the content fluid in the cell S and the cell R, the refractive index of the content fluid is changed accompany with the variation of the composition of the content fluid in the cell S and the cell R. Therefore, the light path of the measuring light which passes through the flow cell 16 will be changed, such that the position of the slit image on the light receiving element 30 is biased from the midmost position. So, the zero glass 28 is rotated to make the slit image be located at the midmost position of the light receiving element 30 (ST.2).

At this time, the rotating angle, stored as the standard value, is read from the storing portion 38. And the standard value is compared with the current rotating angle of the zero glass 28 (ST.3). If the difference between the current rotating angle of the zero glass and the standard value falls within the specified range (e.g., ±1°), it is determined that the rotating angle of the zero glass 28 is in the state that the same solution fills up the two cells, that is, the purging operation is thoroughly performed. If it is determined that the purging operation is thoroughly performed, the flow path is switched to a flow path for analysis process (ST.4). If the difference between the current rotating angle of the zero glass 28 and the standard value does not fall within the specified range, the purging operation is continuously performed.

In this manner, the present invention provides a differential refractive index detector capable of using a set and assured standard to perform the purging operation.

In addition, when the present invention is implemented, the conventional method of performing the purging operation with the specified time and volume can also be used. For example, after conventional purging operation has been performed for at least five minutes, the purging method of the present invention using the rotating angle of the zero glass as the standard is then implemented. Alternatively, after the conventional purging process has been performed for at least 2 ml, then the purging method of the present invention is implemented. Therefore, during the initial stage of the purging operation, even though the following moment exists, i.e., the refractive index of the content fluid in the cell S and cell R is incidentally changed to be the same value, because it is still in the stage of performing the purging operation for at least 5 minutes (or at least 2 ml), it will not determine that the purging operation is finished under an incomplete state.

Furthermore, if the temperature for the cell of the flow cell can be adjusted, 1 minute can be taken as a cycle to enable the set temperature for changing at a sequence of 40° C., 41° C., 40° C., 41° C. . . . , and meanwhile, the purging operation of the present invention is performed also. For the liquid combination with the same refractive index under a certain temperature but different temperature indexes for the refractive index, the purging operation performed by the above method is effective. The temperature is made to change while the determination is performed. Even though under a certain temperature (40° C. here) for making the rotating angle of the zero glass is the same as the standard value, but under another temperature (41° C. here), the rotating angle of the zero glass is not limited to being the same as the reference value. After the composition of the content fluid in the cell S and cell R becomes totally the same, under the above two temperatures, the difference between the rotating angle of the zero glass and the standard value will be within the specified range. Therefore, the replacement is performed under the condition of variable temperatures until the composition of the content fluid in the cell S and cell R becomes the same, so as to practically perform the purging operation thoroughly.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A differential refractive index detector, comprising:
   a light receiving element, receiving a measuring light to generate a slit image, wherein the measuring light is made to pass through a slit to reach a flow cell for being transmitted as a transmitted light, and then, by means of being reflected by a reflecting mirror, the transmitted light is made to re-transmit through the flow cell, and in the flow cell, a sample solution passes through one cell of two cells spaced apart by a spacer inclined with respect to an optical axis of the measuring light, and a reference solution passes through the other cell;
   a zero glass, making the slit image parallelly move on the light receiving element;
   a zero glass driving unit, making the zero glass rotate; and a storing portion, storing a rotating angle of the zero glass when the same solution fills up the two cells.

2. The differential refractive index detector as claimed in claim 1, further comprising:

a determining portion, comparing a current rotating angle of the zero glass with the rotating angle of the zero glass stored in the storing portion during a purging operation of replacing the reference solution of the flow cell, wherein when the difference between the two angles falls into a specified range, the purging operation is finished.

3. The differential refractive index detector as claimed in claim 2, wherein the specified range is between −1° and −1°.

4. A liquid chromatograph, comprising:

a column;

a liquid supply device, supplying a mobile phase into the column;

a sample introducing device, disposed between the column and the liquid supply device; and the differential refractive index detector as claimed in claim 1.

5. The liquid chromatograph as claimed in claim 4, further comprising:

a determining portion, comparing a current rotating angle of the zero glass with the rotating angle of the zero glass stored in the storing portion during a purging operation of replacing the reference solution of the flow cell, wherein when the difference between the two angles falls into a specified range, the purging operation is finished.

6. The liquid chromatograph as claimed in claim 5, wherein the specified range is between −1.degree. and +1.degree.

7. A purging method, suitable for purging a flow cell of a differential refractive index detector, wherein the differential refractive index detector comprises: a light receiving element, receiving a measuring light to generate a slit image, wherein the measuring light is made to pass through a slit to reach the flow cell for being transmitted as a transmitted light, and then, by means of being reflected by a reflecting mirror, the transmitted light is made to re-transmit through the flow cell, and in the flow cell, a sample solution passes through one cell of two cells spaced apart by a spacer inclined with respect to an optical axis of the measuring light, and a reference solution passes through the other cell; a zero glass, making the slit image parallelly move on the light receiving element; and a zero glass driving unit, making the zero glass rotate;

the purging method comprising:

storing a rotating angle of the zero glass in a storing portion when the same solution fills up the two cells; and comparing a current rotating angle of the zero glass with the rotating angle of the zero glass stored in the storing portion during a purging operation of replacing the reference solution of the flow cell, wherein when the difference between the two angles falls into a specified range, the purging operation is finished.

8. The purging method as claimed in claim 7, wherein the specified range is between −1° and +1°.

9. The purging method as claimed in claim 7, wherein before storing the rotating angle of the zero glass when the same solution fills up the two cells, the purging method further comprises:

performing the purging operation on the two cells for a specified time period or at a specified fluid volume.

10. The purging method as claimed in claim 7, further comprising: adjusting a temperature of the flow cell.

* * * * *